United States Patent [19]

Gygax et al.

[11] Patent Number: 6,067,842

[45] Date of Patent: May 30, 2000

[54] COMPUTER-CONTROLLED OLFACTOMETER

[75] Inventors: Hansruedi Gygax, Bad Ragaz; Christian Montagner, Zürich; Norbert Neuner-Jehle, Jona, all of Switzerland

[73] Assignee: Roche Vitamins Inc., Nutley, N.J.

[21] Appl. No.: 09/090,778

[22] Filed: Jun. 4, 1998

[30] Foreign Application Priority Data

Jun. 5, 1997 [EP] European Pat. Off. .............. 97109079
Jun. 23, 1997 [EP] European Pat. Off. .............. 97110247

[51] Int. Cl.[7] .............................. G01N 1/26; G01N 1/38; G01N 31/00
[52] U.S. Cl. ........................................................... 73/23.34
[58] Field of Search ............................................ 73/23.34

[56] References Cited

U.S. PATENT DOCUMENTS

| | | | |
|---|---|---|---|
| 2,837,912 | 6/1958 | Moncrieff | 73/23.34 |
| 3,618,359 | 11/1971 | Randebrock et al. | 73/23.34 |
| 3,882,713 | 5/1975 | Nishida et al. | 73/23.34 |
| 3,902,851 | 9/1975 | Dravnieks | 73/23.34 |
| 4,520,651 | 6/1985 | Litman | 73/23.34 |
| 5,198,155 | 3/1993 | Etzweiler et al. | 73/23.34 X |
| 5,627,307 | 5/1997 | Hayashi | 73/23.34 |
| 5,767,385 | 6/1998 | Bundy et al. | 73/23.34 |

OTHER PUBLICATIONS

S. F. Hallowell et al., Qualitative/Semi Qualitative Chemical Characterization of the Auburn D1 Factometer. *Cargo Inspection Technologies*, SPIE, vol. 2276 (1994), 437–48

*Primary Examiner*—Daniel S. Larkin
*Attorney, Agent, or Firm*—Mark E. Waddell; Stephen M. Haracz; Bryan Cave LLP

[57] ABSTRACT

An olfactometer has a sniffing port, a sample supply for generating a sample flow constituted by a carrier gas and sample head space from a saturation chamber and for supplying the sample flow to the sniffing port, a carrier gas supply, and mixer for predetermined dilution of the sample flow. The carrier gas supply includes mass flow controllers with variable flow rates disposed before the saturation chamber for providing variable carrier gas flow to the saturation chamber. A multiplicity of capillaries of different diameter connect the mixing means with the sniffing port via individual injectors. A computer may be interphased with the olfactometer to regulate the amount of sample and/or carrier gas in the sample flow.

2 Claims, 2 Drawing Sheets

COMPUTER-CONTROLLED OLFACTOMETER

FIELD OF THE INVENTION

The present invention relates to an olfactometer comprising a sniffing port, sample supply means for supplying a sample flow to the sniffing port, carrier gas supply means, and mixing means for predetermined dilution of a sample flow.

BACKGROUND OF THE INVENTION

Olfactometers are instruments capable of exactly dosing a portion of the gaseous phase which is present due to the vapor pressure of a sample or in the form of a liquid or a solid, especially an odorant. Generally in all fields, olfactometers are desired which cover a large dynamic range with a very high accuracy.

An apparatus capable of covering a large dynamic range with a very high accuracy is known from S. F. Hallowell et al., Cargo Inspection Technologies, SPIE Vol 2276 (1994), 437–448. This publication discloses an apparatus which has been developed at the Auburn University and was used to study and to train dogs for explosives detection. It is based on a five-fold dilution cascade.

A compressor delivers air at a constant pressure through a filter and is split in two main channels one of which provides odor-free air used for dilution purposes and the other is used as sample carrier. The sample free air is distributed to five mass flow controllers, which in parallel deliver on five different channels air at a constant flow rate. The sample carrier is passed through mass flow controllers with a variable flow rate. After passing the saturation chamber, the carrier gas is split in two new channels, either to reach the sniff-port via passing a valve or to be further diluted by passing again a variable mass flow controller prior to being mixed with sample free air. Five identical dilution cascades are available of which the theoretical dilution limit is 1:1000 per cascade and would enable a dynamic range of $1:10^{12}$. It was shown experimentally that a dilution range of 1:100 per cascade (range $<10^8$) which only is obtained stepwise.

An important drawback of this system is the obvious path of the sample flow through the mass flow controller units as well as through the valves. The main contamination source of the system is found there. The publication explicitly mentions decontamination procedures. The fact that a mass flow controller is controlled by hot wire detectors, requires calibration data for each gas composition. This makes it impossible to calibrate the system in an exact way. In addition, each inaccuracy in a previous cascade can be amplified by the following dilution step according to error evolution laws.

Moreover, this known olfactometer has only one channel and is, therefore, not capable of performing comparison experiments. Due to the manual operation of the mass flow controllers it is not possible to have a fast and pulse-like stimulus delivery.

SUMMARY OF THE INVENTION

Accordingly, the present invention provides a carrier gas supply means which includes a mass flow control means for feeding a carrier gas flow to a saturation chamber, and a connecting member for conveying a sample flow from the saturation chamber to a sniffing port. The connecting member may be a plurality of capillaries, and the capillaries may have different diameters. The mass flow control means may provide a variable carrier gas flow to the saturation chamber which would contain a sample for interacting with the carrier gas and for creating the sample gas flow. The sample flow would include, and preferably consist of, a carrier gas and a sample head space.

A mixing means may be provided for mixing and diluting a sample flow. The capillaries connect the mixing means and the sniffing port, and an injection member may be positioned to inject the sample flow from the capillaries into the sniffing port. The injection member, preferably, has one injection port for each capillary for injecting a sample flow into the sniffing port.

Thus, the present invention provides an olfactometer which includes a sniffing port, a sample supply means for generating and/or supplying a sample flow from a saturation/sample chamber to the sniffing port, a carrier gas supply means, and a mixing means for preparing a predetermined dilution of the sample flow.

The amount of sample flow and/or carrier gas is controlled by a computer control means.

DETAILED DESCRIPTION OF THE INVENTION

The object of the present invention is to provide an olfactometer which is fast, exact, easy to use, adapted for multichannel arrangements, and which does not have the disadvantages of the known olfactometers.

This is achieved by an olfactometer of the above-described kind, wherein the carrier gas supply means comprises a mass flow controlling means with variable flow rate disposed before the saturation chamber for providing variable carrier gas flow to the saturation chamber and by a multiplicity of capillaries of different diameter connecting the mixing means with the sniffing port via individual injection means.

The success of a threshold olfactometer of the present invention in applications using odorants depends on its dilution capacity and the sample presentation. A very large continuous dynamic dilution range as well as a perfectly memory-free on/off- switching of the odorous stimulus are the key parameters of the present invention that fulfills these requirements.

According to a preferred embodiment of the invention, the dosage of the sample is computer controlled and is available in the form of a self-instructing measurement protocol operating as a virtual instrument which guarantees identical measurement conditions for various sensorial measurements. This embodiment of the invention requires only a minimumally trained panelist.

The detailed description of the invention, of course, includes and is further illustrated with reference to the following drawings.

BRIEF DESCRIPTION OF THE DRAWINGS

In the following a preferred embodiment of the invention is described with reference to the accompanying drawings.

DETAILED DESCRIPTION OF THE DRAWINGS

Figure 1:
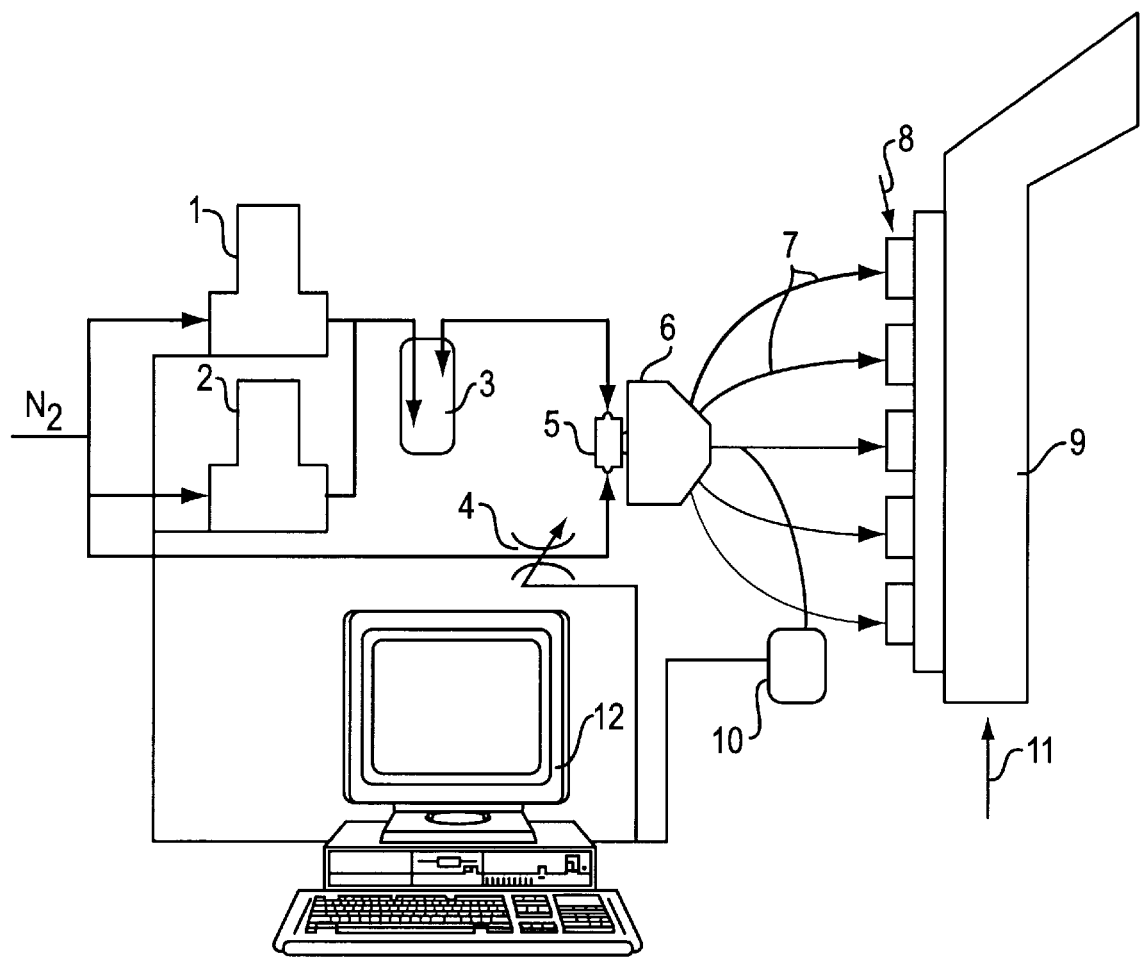
FIG. 1 illustrates a schematical diagram of an olfactometer according to the invention.

The apparatus illustrated in FIG. 1 enables one to perform experiments at a high technical level taking into account important aspects of sensory measurements. It offers a continuously tunable dynamic range of 10% of the saturated headspace concentration down to $10^{-8}$.

The flow of the analyte channel is regulated by two mass flow controllers 1, 2 which are positioned at a position before the saturation chamber 3. Mass flow controller 1 supplies air for higher sample flows and has a range of 50:1000 ml/min whereas mass flow controller 2 has a range of 1:50 ml/min.

The sample carrier gas is introduced from the saturation chamber 3 into the mixing chamber 6 which is connected with a second gas inlet for introducing nitrogen for diluting the sample carrier gas. The final mixing of the sample carrier gas and nitrogen is achieved in a T-junction followed by a mixing restriction 5. A continuous dilution is achieved from a maximum level of 1:1 down to 1:1000.

The amount of nitrogen introduced is controlled by a valve 4 which is driven by the output signal calculated from a PD (proportional, differential) regulation system which uses the signal from a pressure sensor 10 as input. The pressure is measured in the mixing chamber and monitored by a computer 12. A constant pressure in the mixing chamber is important for a constant flow through outlets 7. The outlets may be glass capillaries. The diameters of these outlets are chosen in such a way, that highly accurate flow rates are available in a range of 1:1 to 1:10000.

The sample carrier gas can be selectively injected by a computer controlled injection mechanism 8 from the mixing chamber 6 to the outlets 7 and into the sniffing port 9 where it is continuously mixed with a gas flow 11 having a constant flow rate of 10 l/min. This is approximately equal to the amount of air breathed by a human. The measurement program is responsible for selecting the right dilution level and the necessary capillary in order to obtain a continuously accessible dilution range of 1:10,000,000.

In the present invention, sources of contamination are reduced to a minimum in a very efficient way. Controlling the flow to the saturation chamber ensures that neither the mass flow controller nor the valve is ever in touch with an odorous molecule.

After fine-machining and honing, the stainless steel surfaces of all critical elements, are electro-polished (mixing chamber, injection mechanism) giving memory-free measurement conditions. The temperature of the mixing chamber itself can be raised by a few degrees compared to ambient temperature when low volatile compounds have to be measured. A complete cleaning procedure can be done by disassembling the mixing chamber, capillaries and the injection mechanism and by heating them in an oven (similar to GC-column purification).

Figure 2A:
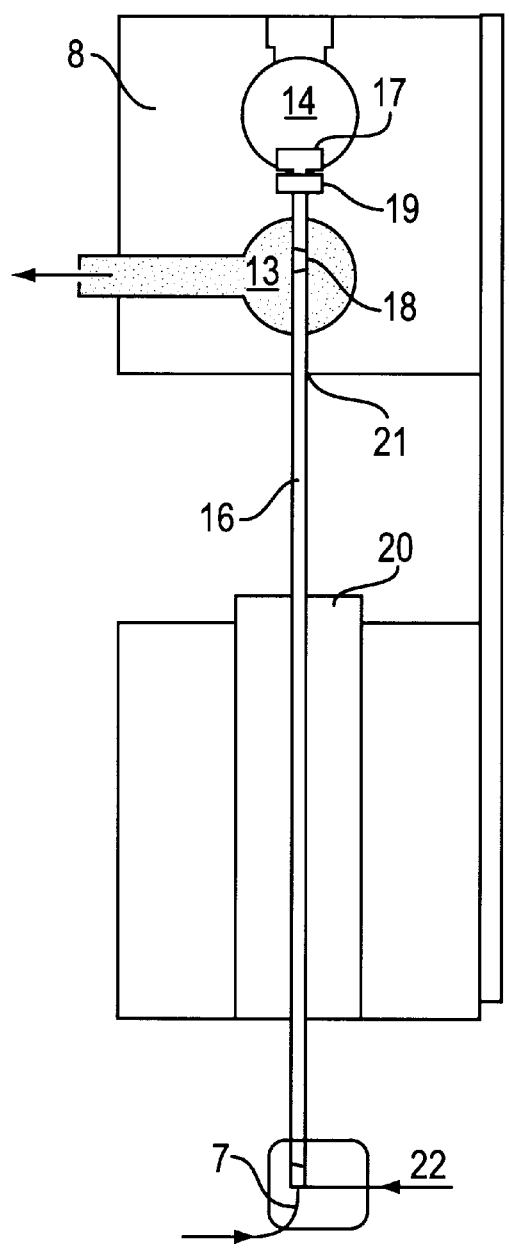
FIG. 2 illustrates cross-sectional views of the injection blocks in two different operating positions.

As illustrated in FIG. 2, the final dilution step is done as previously mentioned, by injecting the sample flow from a capillary into the transport channel 13 of the sniff port by means of an injection block. The injection block 8 comprises a cube (200×25×20 mm) having two longitudinally machined holes, i.e. an exhaust line 13 and a transport line 14 to the sniff port 9. The block 8 contains six individual injection systems for the glass capillaries. The two longitudinal holes are drilled in the horizontal center of the block but are vertically connected through small guiding holes which are machined along the vertical axis.

Adapter capillaries 16 are capped 17 but have outlets 18 which are positioned a few mm from the top of the apparatus. Between the top and sample inlets O-ring seals 19 are inserted in order to prevent the sample stream from traveling into the transport channel while the adapter-capillaries are held in the off-position shown in FIG. 2a. In the off-position) the capillary outlet is flushed directly into the exhaust line. Holes 21 are sealed with teflon. The adapter-capillaries 16 in fact are used for mechanical protection of the glass capillaries 7 which are delicate and constitute a well-calibrated system.

Figure 2B:
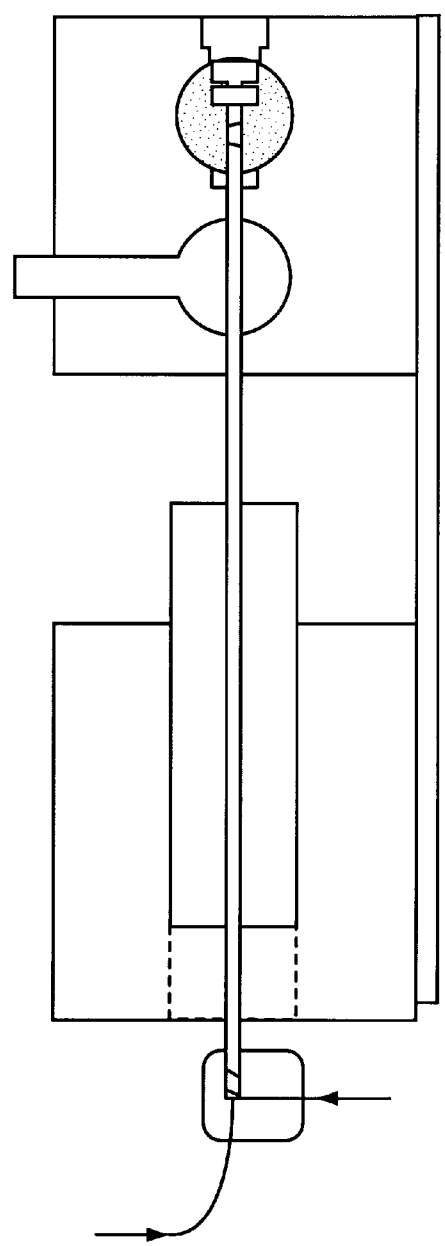

A computer-controlled pneumatic compact-cylinder 20 switches each adapter capillary from the off- to the on-position (see FIG. 2b). Introducing an adjusted make up gas flow (nitrogen) from the lower end 22 of the adapter-capillary 16 makes sure that even for the lowest flow rates measured at the smallest glass-capillary the sample reaches the transport line 14 in the same time as measured on the larger glass-capillaries.

A flush-line constantly purges the O-ring-seal 19 against the flow-direction of the sample carrier gas which ensures that no traces of the sample can reach the transport line 14. An optimum "blank" is achieved when all injection units are switched to the "off-position". Intensity rating or ranking is well known in sensory research and several measurement methods have been developed. Magnitude estimation, reference scaling and category scaling are the most popular ones. Recently, the labelled magnitude scale has been presented and compared to magnitude estimation.

Operations on the olfactometer are computer controlled and the instrument control has been developed under LabVIEW. So called virtual instruments (VI's) are programmed and displayed on the screen if necessary. On such a VI, the operater can set, for example, a desired concentration which is then delivered from the olfactometer. The flexibility of the software allows one to summarize any kind of measurement sequence as a measurement protocol.

A very fast and universal method of measuring the dose/response behavior of odorous substances has been successfully applied using the labelled magnitude scale (LMS). The measured and fitted values can be matched to the ASTM (American Soc. for Testing and Materials) values and any other substance can be compared to the standard. For example, an evaluation of linalool shows an increased slope of the dose/response curve.

Intensity matching experiments can be carried out simultaneously on two modules. This kind of measurement allows the determination of the just notable differences at any concentration level in the supra-threshold regime of an odorant.

Adaptation phenomena can be measured in a separate measurement protocol. The measurement protocol uses the following sequence:

first sequence according to dose/response curve measurement using LMS, and second sequence is the same but prior to the evaluation of the delivered sample the panellists nose is exposed 5 seconds to a very high dose of the same odorant.

The supra-threshold olfactometer according to the present invention has a flexible design which allows the olfactometer to attach different sample saturation chambers. It is possible to perform intensity measurements on applied systems, such as fragrances deposited on laundry etc. These measurements allow a fast comparison of substantivity of different products.

While the invention has been illustrated and described with respect to illustrative embodiments and modes of practice, it will be apparent to those skilled in the art that various modifications and improvements may be made without departing from the scope and spirit of the invention.

Accordingly, the invention is not to be limited by the illustrative embodiments and modes of practice.

We claim:

1. An olfactometer comprising: a sniffing port, sample supply means for generating a sample flow constituted by a carrier gas and sample head space from a saturation chamber and supplying the sample flow to the sniffing port, carrier gas supply means, and mixing means for predetermined dilution of the sample flow, characterized in that the carrier gas supply means comprises mass flow controlling means with variable flow rate disposed before the saturation chamber for providing variable carrier gas flow to the saturation chamber and by a multiplicity of capillaries of different diameter connecting the mixing means with the sniffing port via individual injection means.

2. An olfactometer according to claim 1 characterized by computer control means for controlling dosages.

* * * * *

UNITED STATES PATENT AND TRADEMARK OFFICE
CERTIFICATE OF CORRECTION

PATENT NO. : 6,067,842
DATED : May 30, 2000
INVENTOR(S) : Hansruedi GYGAX, et al.

It is certified that error appears in the above-identified patent and that said Letters Patent is hereby corrected as shown below:

On the title page:

At[73] Assignee, delete "Roche Vitamins Inc., Nutley, N.J."

and

Insert:-- Givaudan-Roure (International) SA, A Swiss Company, Vernier-Geneve, Switzerland--

Signed and Sealed this

Eighth Day of May, 2001

NICHOLAS P. GODICI

*Attest:*

*Attesting Officer*           Acting Director of the United States Patent and Trademark Office